US011594307B2

(12) United States Patent
Eteminan et al.

(10) Patent No.: US 11,594,307 B2
(45) Date of Patent: Feb. 28, 2023

(54) AUTOMATIC SELF-DOCUMENTATION IN A MOBILE-NATIVE CLINICAL TRIAL OPERATIONS SYSTEM AND SERVICE SUITE

(71) Applicant: Laboratory Corporation of America Holdings, Burlington, NC (US)

(72) Inventors: Isaac Eshagh Eteminan, Rancho Santa Fe, CA (US); James William Bishop, Jr., Reno, NV (US); Marco Carosi, Rome (IT); Alessandro Salimbeni, Rome (IT)

(73) Assignee: Laboratory Corporation of America Holdings, Burlington, NC (US)

( * ) Notice: Subject to any disclaimer, the term of this patent is extended or adjusted under 35 U.S.C. 154(b) by 0 days.

(21) Appl. No.: 16/818,634

(22) Filed: Mar. 13, 2020

(65) Prior Publication Data
US 2020/0219593 A1 Jul. 9, 2020

Related U.S. Application Data

(63) Continuation-in-part of application No. 16/778,665, filed on Jan. 31, 2020, and a continuation-in-part of
(Continued)

(51) Int. Cl.
*G16H 10/20* (2018.01)
*G16H 10/60* (2018.01)
(Continued)

(52) U.S. Cl.
CPC ........... *G16H 10/20* (2018.01); *G06F 3/0482* (2013.01); *G06F 3/04845* (2013.01); *G16H 10/60* (2018.01)

(58) Field of Classification Search
None
See application file for complete search history.

(56) References Cited

U.S. PATENT DOCUMENTS

| 8,397,161 B1 * | 3/2013 | Shah | ..................... G06F 40/154 715/249 |
| 9,075,583 B1 | 7/2015 | Cutter et al. | |
| (Continued) | | | |

OTHER PUBLICATIONS

"Offline File Conflicts with SharePoint Online", CIAOPS, Available Online at https://blog.ciaops.com/2018/02/07/offline-file-conflicts-with-sharepoint-online/, Feb. 7, 2018, 11 pages.
(Continued)

*Primary Examiner* — Jonathan Durant
*Assistant Examiner* — Anne-Marie K Alderson
(74) *Attorney, Agent, or Firm* — Kilpatrick Townsend & Stockton LLP

(57) ABSTRACT

A self-documenting clinical trial operations system and service suite and method, with a clinical trial operation software, a coordinator application and coordinator portal, providing information for the clinical trial operation software, a trial design services module, examining a trial design provided by a coordinator and automatically generating a software specification for a trial operations service suite, a patient application and patient portal generated from the trial design services module, for providing patient information for the clinical trial operation software, a customization option to customize at least one of the patient application and patient portal, a specification option to generate a specification document describing a design of a coordinator-customized patient application, wherein the customization and specification options are provided to the coordinator via the coordinator portal.

18 Claims, 9 Drawing Sheets

Related U.S. Application Data application No. 16/805,683, filed on Feb. 28, 2020, and a continuation-in-part of application No. 16/100,078, filed on Aug. 9, 2018, which is a continuation-in-part of application No. 16/100,094, filed on Aug. 9, 2018.

(60) Provisional application No. 62/612,495, filed on Dec. 31, 2017.

(51) Int. Cl.
*G06F 3/04845* (2022.01)
*G06F 3/0482* (2013.01)

(56) References Cited

U.S. PATENT DOCUMENTS

| | | | |
|---|---|---|---|
| 2003/0158947 A1 | 8/2003 | Bloch et al. | |
| 2003/0208378 A1* | 11/2003 | Thangaraj | G16H 30/40 |
| | | | 705/2 |
| 2004/0006553 A1 | 1/2004 | de Vries et al. | |
| 2004/0024616 A1 | 2/2004 | Spector et al. | |
| 2006/0224421 A1 | 10/2006 | St. Ores et al. | |
| 2007/0067189 A1 | 3/2007 | Boris et al. | |
| 2007/0168916 A1* | 7/2007 | Dahlin | G06Q 10/10 |
| | | | 717/101 |
| 2008/0071575 A1 | 3/2008 | Climax et al. | |
| 2009/0228542 A1 | 9/2009 | Meijer et al. | |
| 2009/0313045 A1 | 12/2009 | Boyce | |
| 2011/0125448 A1* | 5/2011 | Jung | G06F 11/3684 |
| | | | 702/108 |
| 2012/0259647 A1 | 10/2012 | Syed et al. | |
| 2013/0185096 A1 | 7/2013 | Giusti et al. | |
| 2014/0108054 A1 | 4/2014 | Udani | |
| 2014/0142984 A1 | 5/2014 | Wright et al. | |
| 2014/0201138 A1 | 7/2014 | Dorman et al. | |
| 2015/0154382 A1 | 6/2015 | Buckley et al. | |
| 2015/0331997 A1 | 11/2015 | Joao | |
| 2016/0110523 A1 | 4/2016 | Francois | |
| 2016/0147951 A1 | 5/2016 | Francois et al. | |
| 2016/0261705 A1 | 9/2016 | Lewandowski | |
| 2017/0039324 A1 | 2/2017 | Francois et al. | |
| 2017/0041205 A1 | 2/2017 | Rangel et al. | |
| 2017/0161313 A1 | 6/2017 | Ritter | |
| 2018/0174675 A1 | 6/2018 | Roy et al. | |
| 2018/0367506 A1 | 12/2018 | Ford et al. | |
| 2019/0012434 A1* | 1/2019 | Frazier | G16H 10/20 |
| 2019/0026786 A1* | 1/2019 | Khoury | G06Q 30/0271 |
| 2019/0131000 A1 | 5/2019 | Fox et al. | |

OTHER PUBLICATIONS

U.S. Appl. No. 16/778,665, Non-Final Office Action, dated May 7, 2021, 32 pages.
U.S. Appl. No. 16/805,683, Non-Final Office Action, dated May 7, 2021, 39 pages.
U.S. Appl. No. 16/100,078, Final Office Action, dated Jan. 14, 2021, 59 pages.
U.S. Appl. No. 16/100,078, Non-Final Office Action, dated May 11, 2020, 48 pages.
U.S. Appl. No. 16/100,094, Final Office Action, dated Jan. 14, 2021, 53 pages.
U.S. Appl. No. 16/100,094, Non-Final Office Action, dated May 11, 2020, 48 pages.
U.S. Appl. No. 16/100,078, Non-Final Office Action, dated Nov. 22, 2021, 20 pages.
U.S. Appl. No. 16/100,094, Non-Final Office Action, dated Nov. 22, 2021, 15 pages.
U.S. Appl. No. 16/778,665, Final Office Action, dated Oct. 25, 2021, 36 pages.
"Enterprise Documentation", Flowable Design/Process Editor, Available Online at: documentation.flowable.com, Apr. 8, 2013, 6 pages.
U.S. Appl. No. 16/100,078, Final Office Action, dated Jun. 7, 2022, 15 pages.
U.S. Appl. No. 16/100,094, Final Office Action, dated Jun. 7, 2022, 13 pages.
U.S. Appl. No. 16/778,665, Non-Final Office Action, dated Jun. 9, 2022, 35 pages.
U.S. Appl. No. 16/805,683, Final Office Action, dated Oct. 25, 2021, 53 pages.
U.S. Appl. No. 16/805,683, Non-Final Office Action, dated Jun. 9, 2022, 61 pages.

* cited by examiner

US 11,594,307 B2

AUTOMATIC SELF-DOCUMENTATION IN A MOBILE-NATIVE CLINICAL TRIAL OPERATIONS SYSTEM AND SERVICE SUITE

CROSS-REFERENCE TO RELATED APPLICATIONS

This application is a continuation-in-part of U.S. patent application Ser. No. 16/805,683 filed on Feb. 28, 2020, a continuation-in-part of U.S. patent application Ser. No. 16/778,665 filed on Jan. 31, 2020, and is a continuation-in-part of U.S. patent application Ser. Nos. 16/100,078 and 16/100,094, both filed on Aug. 6, 2018, which both claim the benefit of provisional U.S. patent application No. 62/612,495 filed Dec. 31, 2017. These applications are each incorporated herein by reference in their entireties.

FIELD

This invention relates to clinical trial operations. More particularly, it relates to systems and methods for "automatically" generating clinical trial operations software interfaces, document control, support menus and so forth, from initial trial protocol descriptions.

BACKGROUND

Conventional clinical trial operations systems require, at a minimum, several months of engineering and software development effort to translate a designed trial protocol to a working software system with a full suite of document management, respective interfaces and menus for the trial participants, as well as for the clinicians and coordinators, etc. Because of the software manpower required, the cost and effort to go from clinical trial protocol design to clinical trial protocol implementation is significant.

What is needed, then, is a capability to generate automatically documents such as software specifications and trial protocol descriptions, at any point in the trial design life cycle, thereby representing and communicating the current state of the design for those documents' respective audiences.

SUMMARY

Broadly speaking, one or more embodiments enhance a mobile-native clinical trial operations system/service suite so it can, via direction by a coordinator, for example, automatically generate documents that describe the clinical trial framework as well as automatically generate algorithms, interfaces and menus for use by the patient.

In one aspect of the disclosed embodiment(s), a self-documenting clinical trial operations system is provided, comprising: a clinical trial operation software running on at least one server; a coordinator application and coordinator portal, providing information for the clinical trial operation software; a trial design services module, examining a trial design provided by a coordinator and automatically generating a software specification for a trial operations service suite; a patient application and patient portal generated from the trial design services module, for providing patient information for the clinical trial operation software; a customization option to customize at least one of the patient application and patient portal; a specification option to generate a specification document describing a design of a coordinator-customized patient application, wherein the customization and specification options are provided to the coordinator via the coordinator portal.

In another aspect of the disclosed embodiment(s), the above system is provided, further comprising an entire specification option to generate an entire specification document describing a design of the entire clinical trial operations system, the entire specification option being provided to the coordinator via the coordinator portal; and/or wherein the trial design services module contains an application factory system that automatically generates via a workflow palette and a composition studio's visual programming toolkit, user interface screens for a clinical trial; and/or wherein the application factory system contains a verification engine, the verification engine comprising: an automatic verification framework with a test case result recorder, capturing in a document associated inputs, state changes, outputs, and result status for test cases; a test plan database with at least one of coverage tests with cases targeted at executing logic paths in an object to be verified and document templates, containing standard formats for documents that are generated automatically; an interactive verification framework with a document editor and supporting user interface; a test device library containing testable device models; application objects and application components to be verified; and a verification service which verifies the application objects and application components; and/or further comprising, a build engine with compilation and subsystem linking services; and/or wherein the build engine uses a test coverage generator as a compiler; and/or further comprising, a composition studio providing an ability to develop applications and the application components; and/or further comprising, a document creation request control; and/or wherein the composition studio utilizes a multimedia user interface design toolkit and programming design toolkit.

In yet another aspect of the disclosed embodiment(s), a self-documenting clinical trial operations service suite is provided, comprising: a coordinator application and coordinator portal, providing information for a clinical trial operation software; a trial design services module, examining a trial designed by a coordinator and automatically generating a software specification for an implementation of the trial; a patient application and patient portal generated from the trial design services module, for providing patient information to the clinical trial operation software; a customization option to customize at least one of the patient application and patient portal; a specification option to generate a specification document describing a design of a coordinator-customized patient application, wherein the customization and specification options are provided to the coordinator via the coordinator portal.

In another aspect of the disclosed embodiment(s), the above suite is provided, further comprising an entire specification option to generate an entire specification document describing a design of the entire trial, the entire specification option being provided to the coordinator via the coordinator portal; and/or wherein the trial design services module contains an application factory system that automatically generates via a workflow palette and a composition studio's visual programming toolkit, user interface screens for the trial; and/or wherein the application factory system contains a verification engine, the verification engine comprising: an automatic verification framework with a test case result recorder, capturing in a document associated inputs, state changes, outputs, and result status for test cases; a test plan database with at least one of coverage tests with cases targeted at executing logic paths in an object to be verified and document templates, containing standard formats for documents that are generated automatically; an interactive verification framework with a document editor and supporting user interface; a test device library containing testable device models; application objects and application components to be verified; and a verification service which verifies the application objects and application components; and/or further comprising, a build engine with compilation and subsystem linking services; and/or wherein the build engine uses a test coverage generator as a compiler; and/or a composition studio providing an ability to develop applications and the application components; and/or further comprising, a document creation request control; and/or wherein the composition studio utilizes a multimedia user interface design toolkit and programming design toolkit.

In another aspect of the disclosed embodiment(s), a method of generating a specification document describing a clinical trial operations system is provided, comprising: analyzing via an embedded mobile application factory system, upon request of a coordinator through a coordinator application and a coordinator portal of a trial operations service suite, a design of applications and services of the clinical trial operations system; and recording results of the analysis in a specification document using a template document.

In yet another aspect of the disclosed embodiment(s), the above method is provided, wherein the design of applications and services of the clinical trial operations system is for a patient application; and/or further comprising: iterating over workflows in the design of the patient application to generate traversal paths for each workflow, wherein each traversal path is a function of user input values and simulated to determine an associated sequence of screens for presentation to a user when a traversal path is executed; capturing in the specification document a graph of corresponding flow annotated with each screen presented and the associated user input values; and filtering duplicate results to minimize a length of the specification document; and/or wherein the analyzing and recording steps further comprise: iterating over workflows in a design of all applications, all services, gateways, and analytic modules of the trial operations service suite, to generate traversal paths for each workflow, wherein each traversal path is a function of input values from users, other system elements, and connected external elements, each traversal path being simulated to determine an associated sequence of screens to a user, signals to other system elements, and signals to connected external elements when a traversal path is executed; capturing in the specification document a graph of corresponding flow annotated with each screen presented and signal sent along with associated input values; and filtering duplicate results to minimize a length of the specification document.

The preceding Summary is intended to serve as a brief introduction to various features of some exemplary embodiments. Other embodiments may be implemented in other specific forms without departing from the scope of the disclosure.

BRIEF DESCRIPTION OF THE DRAWINGS

FIG. 7 illustrates an exemplary method whereby a trial operations service suite in a clinical trial operations system may automatically examine the trial design and generate a software specification for the service suite itself and the applications that interact with.

DETAILED DESCRIPTION

Figure 1:
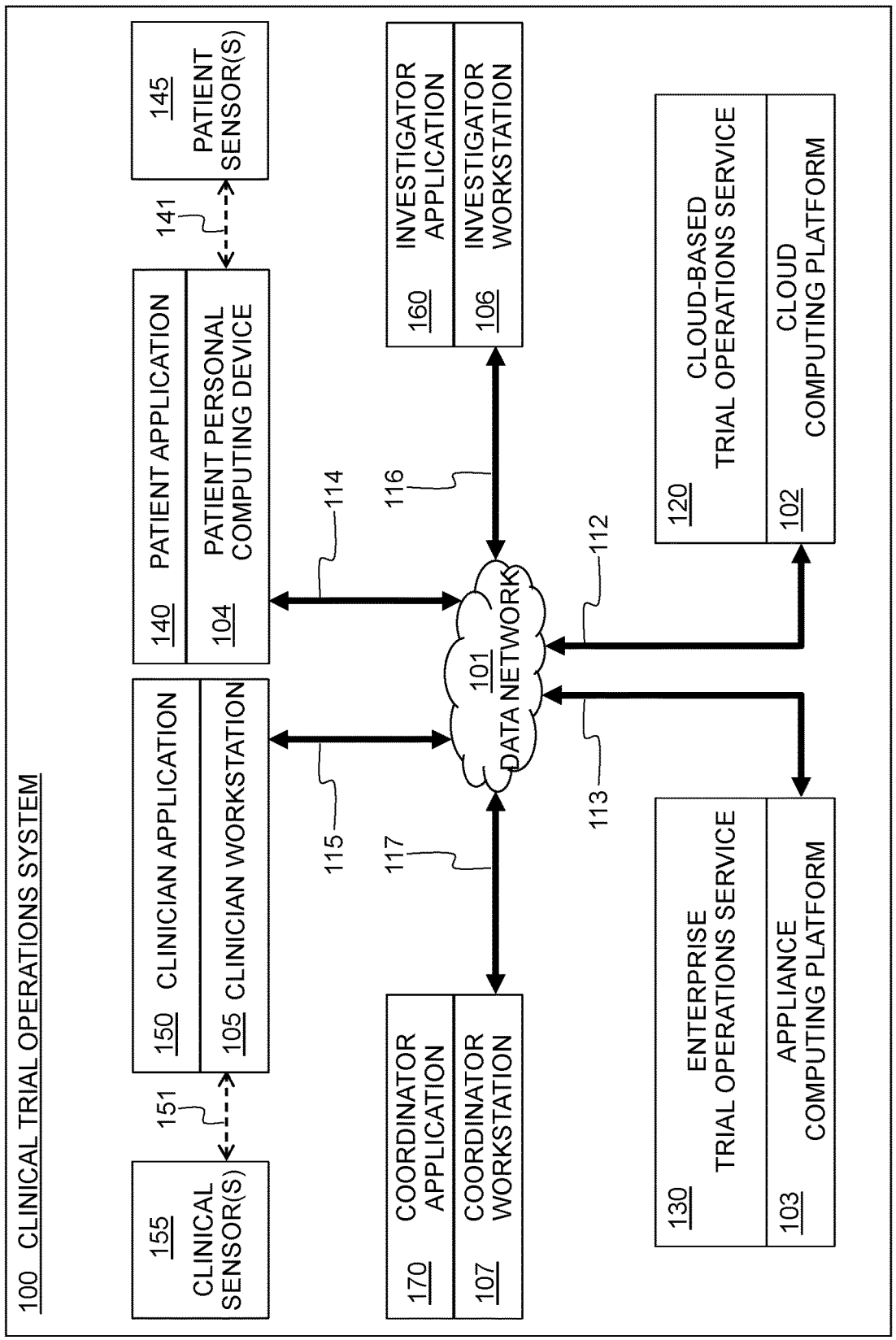
FIG. 1 illustrates a schematic block diagram of an exemplary embodiment of a clinical trial operations system.

The following detailed description describes currently contemplated modes of carrying out exemplary embodiments. The description is not to be taken in a limiting sense but is made merely for the purpose of illustrating the general principles of some embodiments, as the scope of the disclosure is best defined by the appended claims.

Various features are described below that can each be used independently of one another or in combination with other features.

INTRODUCTION

The mobile-native clinical trial operations system and service suite(s) disclosed in U.S. patent application Ser. Nos. 16/100,078 and 16/100,094 (referred to hereinafter as "the base patent application(s)") provides a number of capabilities: such that the patients and their doctors who participate in a drug or device clinical trial benefit from automatic secure collection and storage of relevant data; such that each trial's investigators may securely receive appropriately anonymized (also referred to as de-identified) versions of that data, potentially in real time if allowed by the trial protocol, with automatic secure logging of data access, and may securely record corresponding research activities, observations, and conclusions in a fully traceable lab notebook tied to the trial, its data, and the data access logs; such that each trial's operational coordinators may design trial enrollment (including qualification and consent), engagement, data collection, and other information flow protocols quickly and easily within hours, and automatically create and deploy corresponding web and mobile device applications within minutes, without having to hire an engineering team to spend weeks or months translating the design into software; such that each trial's risk and compliance coordinators may analyze and extract traceability and accountability records as required; and such that all participants are able, if and as permitted by the trial protocol, to communicate with one another securely.

Among the traceability and accountability records not explicitly named in the cited disclosure are detailed descriptions of the trial protocol; that is, a complete set of the screens presented, data collected, decision paths supported, and interactions allowed within a particular clinical trial, with respect to all participants including patients, clinicians, and investigators. Such documents are typically composed during trial design by experts in the subject of the trial as well as the trial design process itself. Two significant uses of the trial design documentation prior to trial commencement are, first, to obtain institutional review board (IRB) approval for the trial and, second, to specify the tools such as software programs to be developed for supporting the trial. In this "waterfall"-style process, the trial protocol can be created and perhaps iteratively refined by trial protocol experts in advance of IRB approval and tool development activity, allowing a confident handoff to the tool development experts.

In view of this, the disclosed mobile-native clinical trial operations system and service suite provides in particular the capability for trial protocol designers to express the trial design directly and naturally using a design studio that can then automatically generate the necessary tools—that is, software in the form of service suite and user applications. In this "agile"-style process, the need for a specification handing off the trial design to tool developers may be bypassed, but the need for a trial protocol description supporting IRB approval remains. Further, even though a software specification document may not be needed for tool development, one may be needed for review of the as-built system service suite and applications—by software engineering professionals in conjunction with IRB approval or regulatory processes.

I. Hardware Architecture

FIG. 1 illustrates a schematic block diagram of a clinical trial operations system 100 according to an exemplary embodiment. FIG. 1 is a copy of FIG. 1 from the base patent application(s), and its description here is also copied therefrom.

Data network 101 may interconnect the various elements of system 100. The network 101 may include one or more private networks as well as one or more public networks including the Internet. Constituent networks may include cellular mobile radio networks using various standards such as LTE; Wi-Fi networks serving public facilities such as airports, shopping centers, hospitals; Wi-Fi networks serving private facilities such as homes, labs, offices, and clinics; wired networks such as Ethernets within private facilities such as homes, labs, offices, and clinics; cable or DSL access networks; and any other form of data network.

Each category of participant may be considered to be a user of corresponding elements in system 100. A patient who participates in a clinical trial supported by system 100 may use a patient personal computing device 104, which may be a mobile device such as a tablet or smartphone, or a traditional computer such as a laptop or desktop, and which may connect to data network 101 via an interface 114 that may be implemented using any of numerous technologies as listed above or otherwise.

Patient application 140 may include software executed by the patient personal computing device 104 that may provide user interface (UI) and operational functions supporting the patient's interaction with system 100. Patient workstation 104 may also execute other software applications that fall outside system 100, in addition to, or in place of, patient application 140. For certain types of study, it may be necessary to incorporate health and environment information from sensors such as blood pressure monitors, heart rate monitors, personal fitness bands, smart watches, smart home products, and/or other similar devices.

For certain kinds of study, it may also be appropriate to incorporate health, event, and environment information from study-specific sensors provided to the patient, such as a custom drug dispenser that detects the time and conditions when a patient consumes a dose. Such devices are represented in the diagram by patient sensor(s) 145. In addition to study-specific sensors, such patient sensors may include biometric sensors (e.g., heart rate monitors, blood pressure sensors, blood sugar sensors, thermometers, etc.), environmental sensors (e.g., humidity sensors, temperature sensors, etc.), and/or event other event sensors. Furthermore, such sensors may include data received from a patient (e.g., indication of pain level or other appropriate factor, logging medication times and/or amounts, etc.).

Patient sensor(s) 145 may communicate with the patient personal computing device 104 via an interface 141 in order to provide sensor readings and related information. For each device represented by patient sensor(s) 145, interface 141 may include a wired connection such as a USB cable, and/or a wireless connection such as Bluetooth or Wi-Fi.

A doctor, advanced practitioner, or nurse who treats or oversees treatment of a patient participating in a clinical trial supported by system 100 may use a clinician workstation 105, which may be a mobile device such as a tablet or smartphone, or a traditional computer such as a laptop or desktop, and which may connect to data network 101 via an interface 115 that may be implemented using any of numerous technologies as listed above or otherwise.

Clinician application 150 may include software executed by clinician workstation 105 that provides UI and operational functions supporting the clinician's interaction with system 100. Clinician workstation 105 may also execute other software applications that fall outside system 100, in addition to, or in place of, clinician application 150.

For certain kinds of study, it may be necessary to incorporate health and environment information from sensors such as blood pressure monitors, heart rate monitors, thermometers, CT scanners, MRI scanners, and/or other diagnostic devices. Such devices are represented in the diagram by clinical sensor(s) 155. Clinical sensor(s) 155 may communicate with clinician workstation 105 via an interface 151 in order to provide sensor readings and related information. For each device represented by clinical sensor(s) 155, interface 151 may include a wired connection such as a USB cable or Ethernet network, a wireless connection such as Bluetooth or a Wi-Fi network, or a combination of such connections.

A technician, scientist, or other researcher who analyzes data and draws conclusions regarding the results of a clinical trial supported by system 100 may use an investigator workstation 106, which may be a mobile device such as a tablet or smartphone, or a traditional computer such as a laptop or desktop, and which may connect to data network 101 via an interface 116 that may be implemented using any of numerous technologies as listed above or otherwise.

Investigator application 160 may include software executed by investigator workstation 106 that provides UI and operational functions supporting the investigator's interaction with system 100. Investigator workstation 106 may also execute other software applications that fall outside system 100, in addition to, or in place of, investigator application 160.

A supervisor, designer, trial manager, site manager, risk manager, compliance manager, or other administrator who oversees one or more aspects of a clinical trial supported by system 100 may use a coordinator workstation 107, which may be a mobile device such as a tablet or smartphone, or a traditional computer such as a laptop or desktop, and which may connect to data network 101 via an interface 117 that may be implemented using any of numerous technologies as listed above or otherwise.

Coordinator application 170 may include software executed by coordinator workstation 107 that provides user interface and operational functions supporting the coordinator's interaction with system 100. Coordinator workstation 107 may also execute other software applications that fall outside system 100, in addition to or in place of coordinator application 170.

The system 100 may utilize a trial operations service that provides capabilities with which each participant may interact via the respective application. A distinct trial operations service may be used for each separate clinical trial in order to ensure strong data privacy protection, even when a single organization is operating multiple trials and therefore multiple trial operations services. Such an approach also prevents propagating any faults that may occur in one instance to other instances, thereby ensuring that no single fault compromises multiple trials.

The example of system 100 includes two kinds of trial operations service, but for any particular trial only one of those types is to be deployed, depending on the preference of the organization operating the trial.

A cloud-based trial operations service 120, which may include software functions executing in a cloud computing platform 102, may be selected by an organization that prefers to outsource its information technology operations to an expert in that field. For example, a biopharmaceutical research lab may prefer not to distract itself from its core competency, or a government research lab may require implementation using the services of a Federal Risk and Authorization Management Program (FedRamp)-approved provider.

An enterprise trial operations service 130, which may include software functions executing in an appliance computing platform 103, may be selected by an organization such as a large company with multiple capabilities that prefers to keep information technology operations in its own facility and network. For example, a medical device manufacturer may already have information technology competency due to the electronic and software-driven nature of its devices. Other reasons may also exist for choosing one or the other deployment option for the trial operations service.

One of ordinary skill in the art will recognize that system 100 may be implemented in various different ways without departing from the scope of the disclosure. For instance, the various elements of the system may be arranged in various different ways. As another example, various devices or elements may be implemented using multiple devices or sub-elements. Likewise, in some embodiments multiple devices or elements may be combined into a single device or element. In addition, various other elements may be included and/or various listed elements may be omitted in some embodiments.

II. Services

Many clinical trials take place in multiple locations, with separate personnel who may or may not interact with one another. In each of the participant categories described above, individual participants may be associated with one or more such locations, or sites, such that data access and communication permissions may be constrained to remain within each site. For example, a coordinator in the trial manager role may have permission to access data for all sites, while a coordinator in a site manager role may only have permission to access data for the assigned site. However, in clinical trial operations system 100 all sites associated with a particular clinical trial are supported by the same trial operations support service 120 or 130, thus ensuring commonality of trial data and procedures across all sites.

Figure 2:
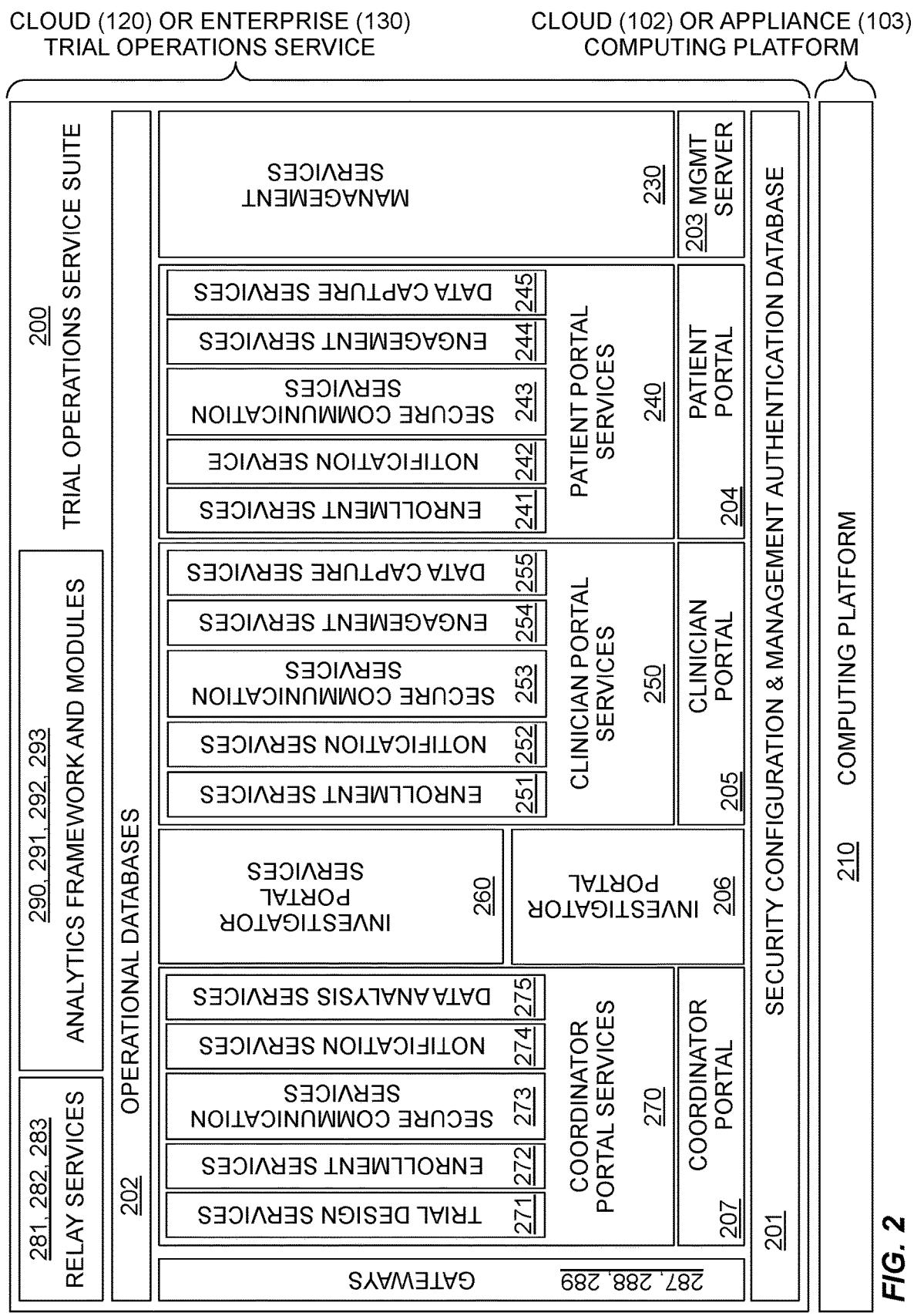
FIG. 2 illustrates a schematic block diagram of an exemplary embodiment of a trial operations service suite in a clinical trial operations system.

Enterprise trial operations service 130 and cloud-based trial operations service 120 may be similar, and both appliance computing platform 103 and cloud computing platform 102 provide similar capabilities. A unified view detailing these is provided in FIG. 2, which illustrates a schematic block diagram for a trial operations service suite 200 and computing platform 210 in a clinical trial operations system according to an exemplary embodiment. FIG. 2 is a composite of FIG. 2 and FIG. 3 from the base patent application(s), and much of its description here is repeated therefrom.

The mapping of trial operations service suite 200 modules to both cloud trial operations service 120 and enterprise trial operations service 130 is represented by the long upper bracket. The mapping of computing platform 210 modules to both cloud computing platform 102 and enterprise computing platform 103 is represented by the short lower bracket. Computing platform 210 is not further detailed here; it may be substantially as detailed in the base patent application(s).

Because clinical trial operations are subject to strict regulatory requirements regarding information security and privacy, computing platform 210 must be carefully selected and configured with features that accommodate those requirements. Encryption of data at rest and in motion, role-based data access permission capabilities, and bulletproof communication stacks are all important. A cloud computing platform 102 may be used only if it explicitly supports HIPAA compliance, which in addition to the features listed above also requires physical security and strong partitioning among customers so unrelated applications cannot interact with one another either intentionally or unintentionally. An organization choosing to deploy trial operations service suite 200 in an appliance computing platform 103 is obliged to satisfy these physical security and related requirements itself.

Security configuration and management authentication database 201 may provide a data repository specifically for information about the particular trial operations service suite 200 and its deployment in computing platform 210. Configuration data may include, but is not limited to, such persistent knowledge as how it relates to the network in which it resides, how the various function modules are deployed across potentially multiple physical and/or virtual computing machines, and licensed capacity. Security configuration data in particular may provide the mathematical basis of trust for establishing communication paths at the level of attaching the services hosted in trial operations service suite 200 to other services elsewhere in the network. Management authentication data may provide the credentials and permissions necessary to protect access to management functions.

Operational databases 202 may provide multiple data repositories specific to the clinical trial supported by trial operations service suite 200. This group of databases is architecturally distinct from security configuration and management authentication databases 201 for reasons of information privacy, data capacity differences, and transaction capacity differences. A detailed description of the specific data modules within operational databases 202 may be found in the base patent application(s).

Beyond that foundation, the functions of trial operations service suite 200 may fall into a few major groups. The first of these includes the management functions, which may provide ways to configure and control the trial operations service suite 200 and the underlying computing platform 210. Management server 203 may form the basis of the management function group, providing a network interface and an operating environment for the various management services. Management server 203 may include such components as a web server, a secure shell interface, a file transfer protocol server, and related capabilities typically used in the management of information technology systems. Management services 230 are not further detailed here; this element may be substantially as detailed in the base patent application(s).

The next major group of functions are the internal relay services 281, 282, and 283, and the external gateways 287, 288, and 289. Relay services provide capabilities for interaction among services of trial operations service suite 200. Gateways provide capabilities for communication and data access between trial operations service suite 200 and affiliated external systems, or among multiple related trial operations service suites 200. These functions may be substantially as detailed in the base patent application(s).

The next major group of functions is the data analytics framework 290 and its modules 2901, 292, and 293. These may provide an environment for automatic processes that analyze different types or multiple types of data as it comes into the system, looking for correlations indicating some important actionable fact. These functions may be substantially as detailed in the base patent application(s).

The final major group of functions in trial operations service suite 200 may provide access for various types of user in the trial community served by trial operations service suite 200. Each user category may be provided with a respective portal 204, 205, 206, or 207, which may include a web server dedicated to that category of users and which may support highly secure information presentation and interaction for multiple users within that category.

Multiple user roles may also be supported within each category, as well as site assignments for each user, depending on data access permissions encoded in a provisioning and authorization data subset of operational databases 202. For each user category, support for a variety of capabilities may be encapsulated within a corresponding set of services 240, 250, 260, or 270 built atop the corresponding portal 204, 205, 206, or 207, partitioned from the others to prevent inappropriate information crossover, and interacting with the corresponding application 140, 150, 160, or 170 of system 100. Each user category's portal and services are described below.

Patient portal 204 and patient portal services 240 may provide access for patients participating in the supported clinical trial, interacting with patient application 140. The patient user category may include user accounts not only for a particular patient participating in a clinical trial, but also any of that patient's family members or representatives such as a formally declared HIPAA agent or a holder of healthcare power of attorney who the patient has designated to have access to the system. Each patient account may have specific permissions to view data, update data, create diary and journal entries, receive notifications, and the like, depending on the corresponding records in a provisioning and authorization data subset of operational databases 202 as established by the patient, or the trial protocol as established by a coordinator. Patient portal 204 may provide, through patient application 140, a base view whereby the patient user can see account status, see overviews of each available service such as whether unviewed notifications exist, and select an available service to activate.

Patient portal services 240 may include any or all of the services shown depending on the requirements of the particular clinical trial being supported by trial operations service suite 200. Additional services not shown or described may also be created within this service framework.

Patient portal services 240 may include a group of enrollment services 241, a notification service 242, a group of secure communication services 243, a group of engagement services 244, and a group of data capture services 245. Each of these services may be substantially as detailed in the base patent application(s).

Clinician portal 205 and clinician portal services 250 may provide access for clinicians with one or more patients participating in the supported clinical trial, interacting with clinician application 150. The clinician user category may include user accounts not only for a doctor treating a particular patient participating in a clinical trial, but also any of that doctor's staff, partners, associated advanced practitioners, or nurses who also participate in treatment or care of a participating patient. Each clinician account may have specific permissions to view data, update data, create diary entries, receive notifications, and the like, depending on the corresponding records in provisioning and authorization data subset of operational databases 202 as established by the primary clinician, or the trial protocol as established by a coordinator.

Clinician portal 205 may provide, through clinician application 150, a base view whereby the clinician user can see account status, see overviews of each available clinician-specific service such as whether unviewed notifications exist and select an available service to activate, view a list of associated patients participating in the supported clinical trial and corresponding overviews of patient-related services, and select a patient and service from that list.

Clinician portal services 250 may include any or all of the services shown depending on the requirements of the particular clinical trial being supported by trial operations service suite 200; additional services not shown or described may also be created within this service framework.

Clinician portal services 250 may include a group of enrollment services 251, a group of notification services 252, a group of secure communication services 253, a group of engagement services 254, and a group of data capture services 255. Each of these services may be substantially as detailed in the base patent application(s).

Investigator portal 206 and investigator portal services 260 may provide access for investigators handling the research and analysis responsibilities in the supported clinical trial, interacting with investigator application 160, and may be substantially as detailed in the base patent application(s).

Coordinator portal 207 and coordinator portal services 270 may provide access for people in charge of managing various aspects of the trial, interacting with coordinator application 170. The coordinator user category may include user accounts for various individuals with distinct or overlapping responsibilities, including but not limited to trial design, everyday trial operations, and compliance. Each coordinator account may have specific permissions to view data, update data, change the trial design, send notifications, and the like, depending on the corresponding records in a provisioning and authorization data subset of operational databases 202 as established by the primary coordinator. Coordinator portal 207 may provide, through coordinator application 170, a base view whereby the coordinator user can see account status, see overviews of each available coordinator-specific service, and select an available service to activate.

Coordinator portal services 270 may include any or all of the services shown depending on the requirements of the particular clinical trial being supported by trial operations service suite 200; additional services not shown or described may also be created within this service framework.

Coordinator portal services 270 may include a group of enrollment services 272, a group of secure communication services 273, a group of notification services 274, and a group of data analysis services 275, all of which may be substantially as detailed in the base patent application(s).

Coordinator portal services 270 may also include a group of trial design services 271, which may support configuration of trial operations service suite 200 for the particular clinical trial being supported. Trial design services 271 may be used both at the beginning of a trial to set its initial design, and during the trial to change aspects of its design that may need adjustment as the trial progresses. Trial design services 271 may provide selections to configure whether specific services are available in each group of portal services 240, 250, and 260, such as which communication modes may be activated, as well as other configuration items such as whether gateways 287, 288, and 289 are active and if so with what other systems they may interoperate, what kind of inter-user communication, notification, and invitation pairings are permitted, and what kind of data analytics are activated.

Trial design services 271 may also provide capabilities for designing detailed user interaction procedures such as screen layouts, order of presentation and text for participant qualification and informed consent protocols, supported sensors both mandatory and optional, sensor data collection schedules, branding imagery and wording, wording of internal and external notification templates, wording of invitation templates, structure of surveys and status queries, structure and emphasis of diary or journal entry templates, structure and emphasis of lab notebook entry templates, supported data access query templates, data access result display formats, and every other aspect of user interaction supported by applications 140, 150, and 160. Trial design services 271 may even alter the look and capabilities of coordinator application 170 itself.

Figure 5:
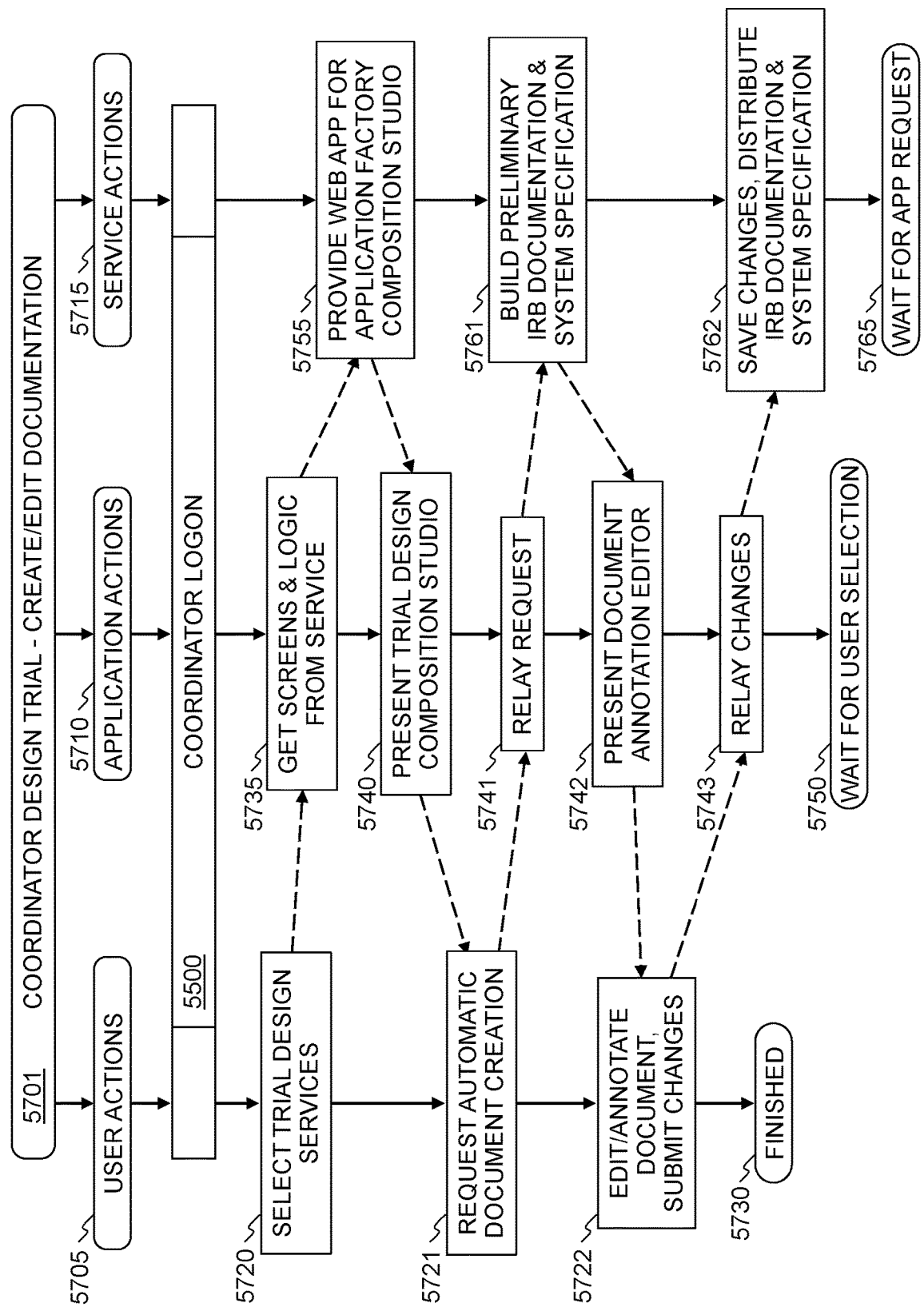
FIG. 5 illustrates a process distributed among a coordinator application, coordinator portal, and other elements of a trial operations service suite in a clinical trial operations system according to an exemplary automatic documentation embodiment.
Figure 7:
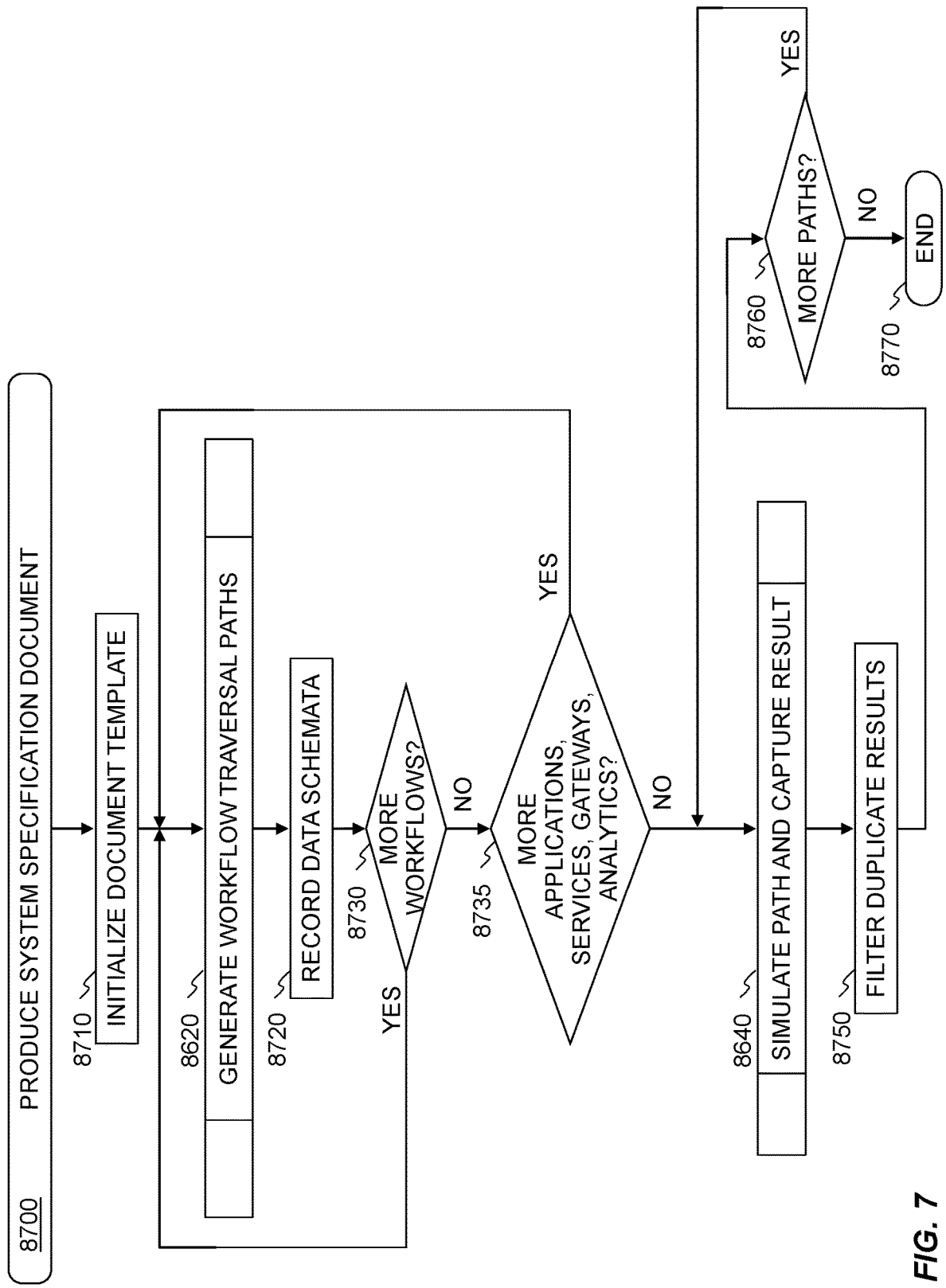
Figure 8:
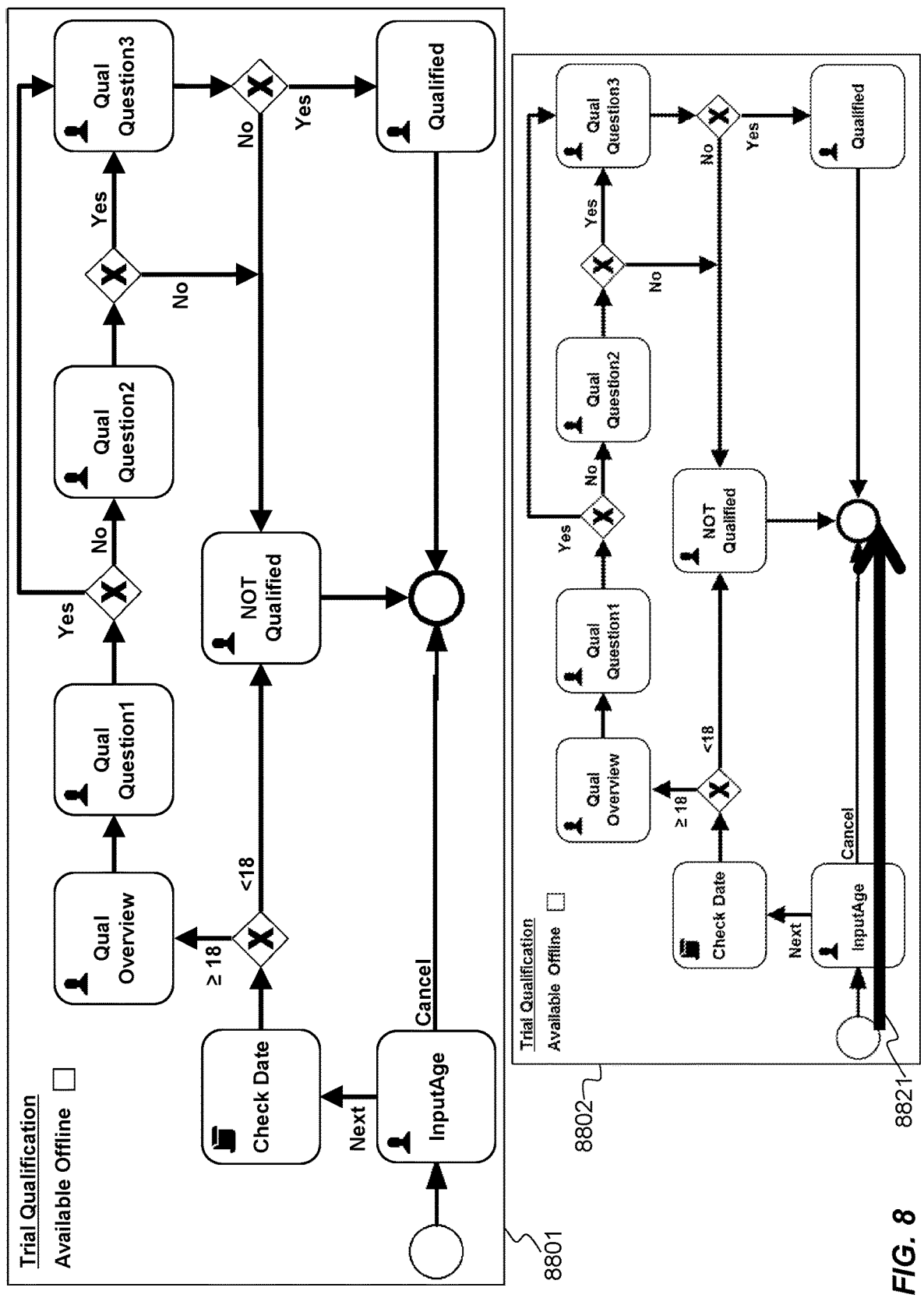
FIG. 8 and FIG. 9 illustrate an exemplary workflow and its traversal paths as may be generated by the methods illustrated in FIG. 6 and FIG. 7.

Trial design services 271 may also provide capabilities for automatically generating external documentation of a particular trial design, in accordance with the present disclosure and described in the context of FIG. 5, FIG. 8, and FIG. 7.

Figure 3:
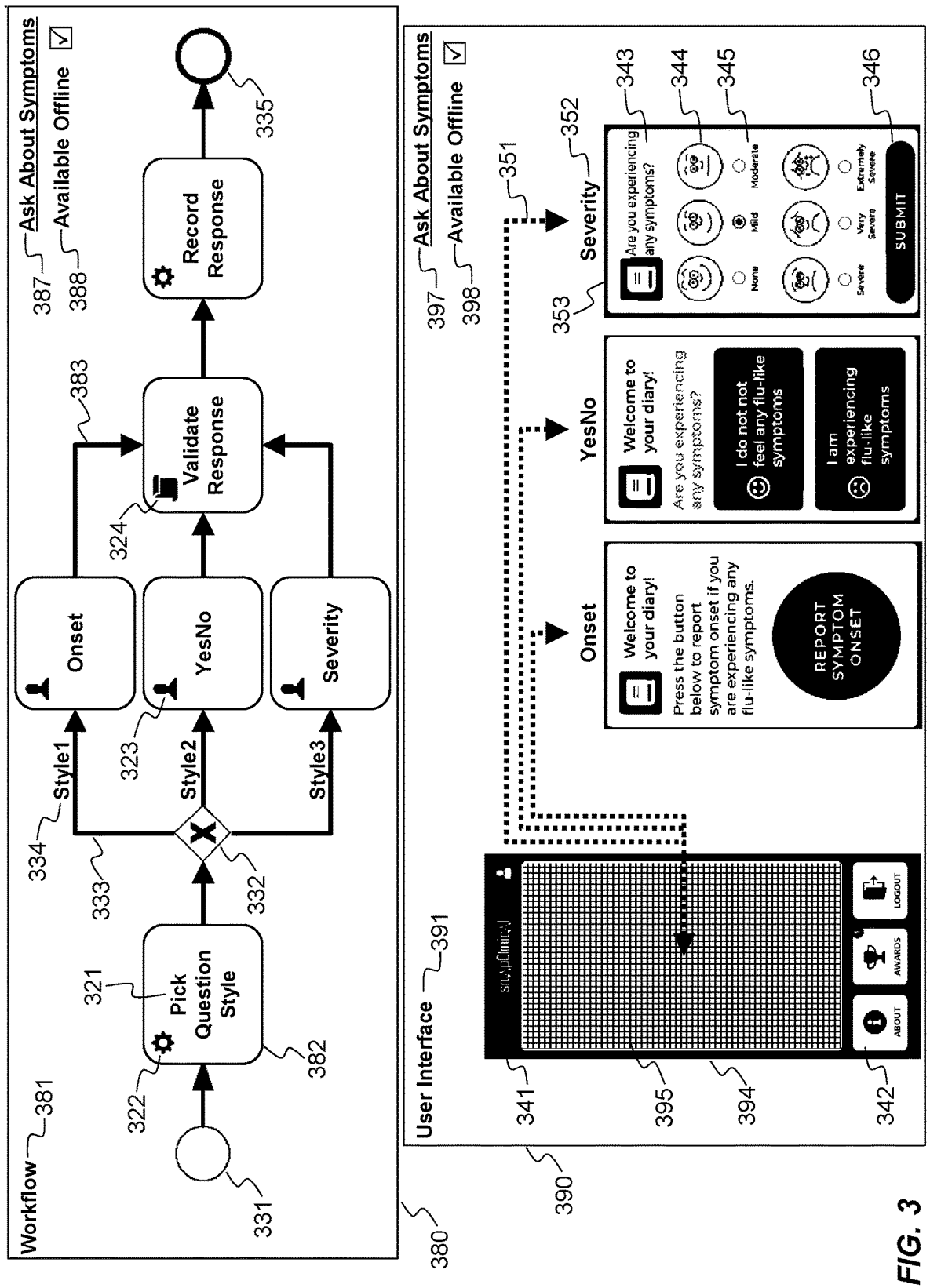
FIG. 3 illustrates an exemplary workflow and corresponding user interface screens which may be included in a web or mobile device application in a clinical trial operations system.

FIG. 3 illustrates an exemplary workflow and corresponding exemplary user interface screens which may be included in a patient application 140. Example workflow 380 may be created using the application factory system embedded in trial design services 271, and customized to a specific clinical trial according to the dictates of its protocol using the Flowable-based workflow palette in conjunction with the composition studio's visual programming toolkit. Similarly, example user interface screens 390 may be created using the application factory system embedded in trial design services 271, and customized to a specific clinical trial according to the dictates of its protocol using the various palettes available in the composition studio's design toolkit. Note that the exact nature of the workflow shown in FIG. 3 is a simple patient questionnaire, which is visibly related by the nature of its depicted imagery and text to the clinical trial field of use pertinent in the present disclosure. However, it is described here in terms of its logical and structural symbology in order to focus on the capability of building relevant workflows rather than on any specific workflow topic. A coordinator user of trial design services 271 may create any number of such workflows and user interfaces to represent the trial protocol, which may then in turn be assembled into patient, clinician, investigator, or coordinator applications 140, 150, 160, or 170 respectively.

The representation of example workflow 380 and its example user interface 390 thus includes a number of symbols with specific meanings in the context of trial design services 271. Workflow label 381 and user interface label 391 distinguish between the logical and graphical specifications, while workflow name 387 and user interface name 397 contain text strings created by the designing coordinator user to distinguish this workflow and its user interface from others. The same value, "Ask About Symptoms" in the example, is shown for both names 387 and 397 to indicate that this workflow 380 and this user interface 390 are related to one another.

Figure 4:
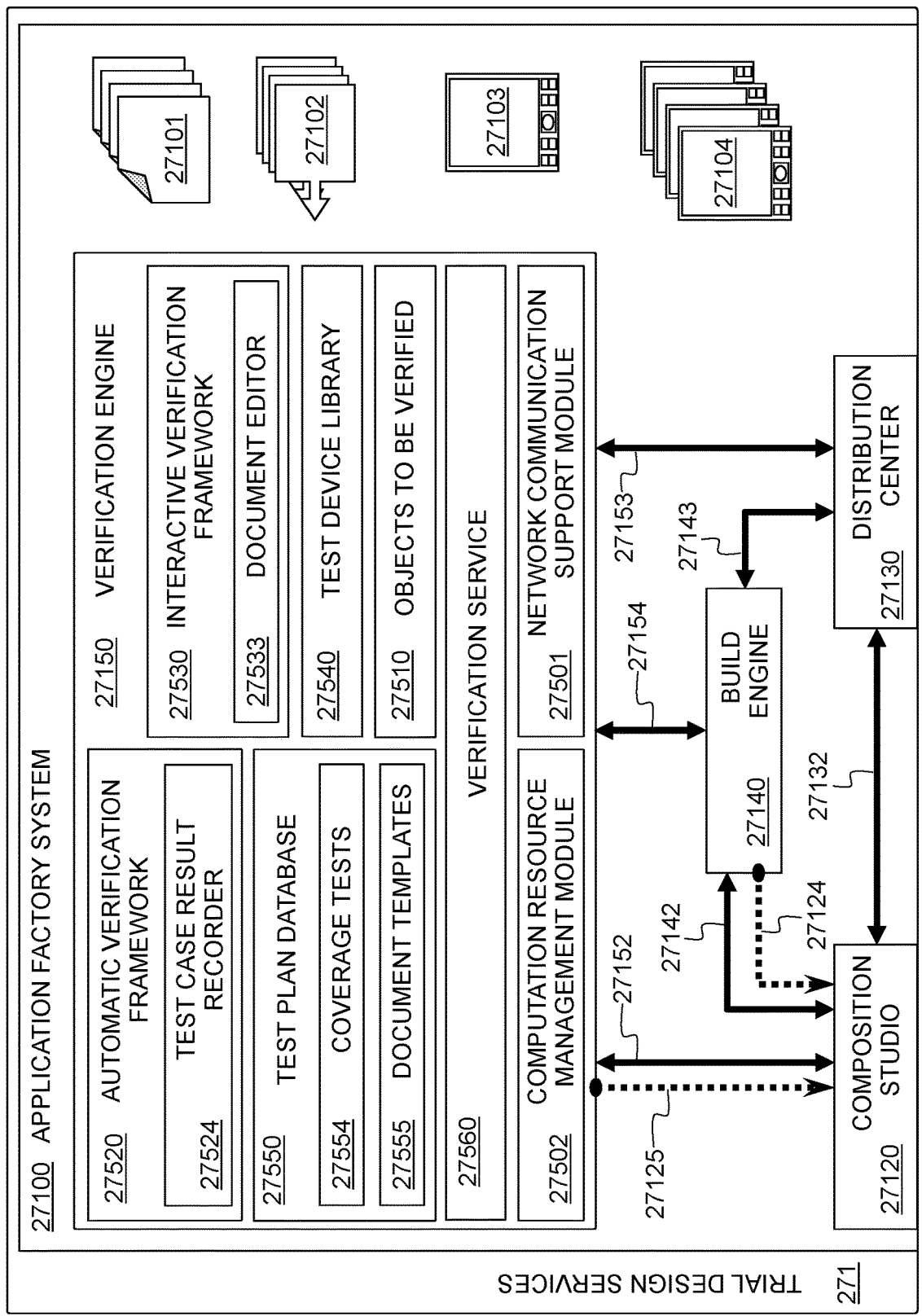
FIG. 4 illustrates a schematic block diagram of an exemplary application factory system disclosed in U.S. Pat. No. 8,719,776, enhanced as disclosed in U.S. patent application Ser. No. 16/100,078, encapsulated within a trial design services element of a trial operations service suite in a clinical trial operations system.

Of particular relevance to the present disclosure are workflow attribute 388 and user interface attribute 398, which both indicate that the elements of this workflow 380 and this user interface 390 are available offline. That is, their structure and content may be pushed to application 140 or 150 for use even when there is no connection to the corresponding portal services 240 or 250. Refer to FIG. 4 and later for additional details on this capability.

The flow aspect of example workflow 380 begins at start symbol 331 and is complete at end symbol 335. Other symbols not shown may represent waiting for a message from an external entity or suspending for a period of time. To get from start to end, a variety of actions, decisions, and transitions may occur. Each action block 382 provides an opportunity for the application implementing example workflow 380 to do something useful, which typically may be summarized using the action block name 321. The actual details of what the action block 382 does may be specified by invoking a composition studio canvas and palette that corresponds to the action block type. The action block name 321 may also match a named element in the corresponding canvas, so as to specify a definitive relationship between the workflow action block and the underlying action. Each transition 383 may provide a time-ordered flow from a start symbol 331 or action block 382 to another action block 382, an end symbol 335, or a decision block 332. Each decision block 332, of which only one is present in FIG. 3, may provide a branch in the flow based on a data item identified by the preceding action block 382. Each possible value of the data item may then be used as a transition name 334 associated with a corresponding named transition 333, such that the decision block 332 directs the flow along the corresponding path according to the selected value. Note that the only type of decision block 332 shown in FIG. 3 is similar in meaning to a CASE statement in a traditional computer programming language. Other decision block types may be used, each one represented using a different symbol not shown, including such common operations as logical and numerical comparisons, as well as a multipath operation that splits the flow into two or more simultaneous sequences.

Three types of action block are depicted here using distinct icons to represent each, and others may be inferred from the composition studio descriptions in the base patent application(s) and in U.S. Pat. No. 8,719,776, which together describe more than this number of canvas/palette combinations. Action block type 322 may manipulate data, such as reading a variable in the type 322 action block 382 labeled "Pick Question Style" or writing a variable in the type 322 action block 382 labeled "Record Response." Within the composition studio of trial design services 271, selecting or creating an action block 382 of type 322 may invoke the data palette of the data and logic canvas in order to specify the pertinent data items and what is to be done with them. It should be noted that multiple "types" of data manipulation can be performed by the composition studio, the types and action coming from linked or incorporated toolkits, non-limiting examples being multimedia user interface design and programming design toolkits, additional examples being found in the base patent application(s). This palette and canvas are not further described here; refer to the aforementioned antecedents for details.

Action block type 323 may cause the presentation of a corresponding screen or subscreen according to the relationship indicated via the action block name 321. Within the composition studio of trial design services 271, selecting or creating an action block 382 of type 323 may invoke the user interface canvas to specify the corresponding user interface elements. More detail regarding the construction of corresponding screens follows in the context of example user interface 390.

Action block type 324 may cause the execution of an algorithm, effectively a subroutine that matches the action block name 321. Within the composition studio of trial design services 271, selecting or creating an action block 382 of type 324 may invoke the logic palette of the data and logic canvas in order to specify the algorithm to be executed. Any operation that may be expressed in the data and logic canvas may be incorporated in the corresponding algorithm; thus an action block 382 of type 324 may perform calculations, interact with other entities through external communication, start or stop sensors or actuators in the mobile device running application 140 or 150, or any other operation available in that portion of the composition studio. This palette and canvas are not further described here; the aforementioned antecedents provide details.

As previously noted, example user interface 390 is associated with example workflow 380 through the common value in their respective names 387 and 397. In the user interface canvas, a coordinator user may arrange passive graphical elements such as text 343 and icons 344, and active graphical elements such as selectors 345 and buttons 346. These arrangements may be grouped into fixed areas such as header 341 and footer 342 so that they appear in every variation of screen 394, or they may be grouped into subscreens 353 linked to a variable area 395 by subscreen relationships 351 so that the appropriate visual and control arrangement may be selected according to workflow logic. Subscreen names 352 would then be used to associate each subscreen 353 with an action block of type 323 by matching its action block name 321.

One skilled in the art will appreciate that the fixed areas header 341 and footer 342 in screen 394 may have as easily been designed using additional variable areas 395 and accompanied by additional subscreens 353 with corresponding name relationships 352 to additional action blocks 382 of type 323. Further, the specific decisions regarding structure and design of a workflow and its user interface are entirely at the coordinator user's discretion and may take any conceivable form, including more or fewer elements in different orders with simpler or more complex logic. Similarly, the values of names 387, 397, 321, 334, and 352, as well as the content and form of graphical elements such as text fields 343, images 344, and buttons 345 and 346, are also design choices that may be exercised by the coordinator user. One skilled in the art will also appreciate that the range of logic and graphic elements is not limited to those described here. The full set of capabilities supported by the application factory system embedded in trial design services 271 may be utilized in designing real workflows and user interfaces for a specific clinical trial. Further, it should be noted that the specific graphic style of each symbol depicted in FIG. 3 is important only to the extent that it evokes the workflow or user interface element it is meant to represent. Other symbols and symbol positions may be used equally as well within the scope of the present disclosure.

In an exemplary embodiment, trial design services 271 may be implemented by embedding in trial operations service suite 200 an enhanced version of the application factory system disclosed in U.S. Pat. No. 8,719,776, which is incorporated herein by reference. Enhancements in this regard may be substantially as detailed in U.S. patent application Ser. Nos. 16/100,078 and 16/100,094 (the base patent applications), as well as the further enhancements provided in the present disclosure regarding automatic documentation generation described in the context of FIG. 4, FIG. 5, FIG. 6, and FIG. 7. Additional detail regarding this embedment as well as detail regarding the automatic document generation feature are shown in FIG. 4.

Each of the application factory system elements, numbered 1xx in FIG. 1 of U.S. Pat. No. 8,719,776, is depicted here in FIG. 4 numbered 271xx, highlighting the embedment in trial design services 271. Certain elements, particularly the major subsystems composition studio 27120, distribution center 27130, and build engine 27140, as well as the interfaces among them 27124, 27142, 27132, and 27143 may be substantially as described in U.S. Pat. No. 8,719,776, where they are numbered 120, 130, 140, 124, 142, 132, and 143 respectively, as enhanced by the corresponding descriptions in the base patent application(s). Similarly, the various applications 27101, application components 27102, generic mobile device model 27103, and specific mobile device models 27104 may be substantially as described in U.S. Pat. No. 8,719,776, where they are numbered 101, 102, 103, and 104 respectively, except that in the present disclosure applications 27101 and application components 27102 may be specifically pertinent to the field of clinical trial support, where their archetypes 101 and 102 may be pertinent to any field.

Verification engine 27150 is enhanced in the present disclosure, compared to its archetype verification engine 150 in U.S. Pat. No. 8,719,776. While structurally quite similar, each element of verification engine 27150 includes additional functional and data handling capabilities with respect to the new document generation and editing feature. Pertinent functional elements are shown in the figure, while data handling enhancements are pervasive and not specifically depicted. The latter may generally occur as additional fields in data structures used inside each function as well as in communication among the functions and on interfaces 27125, 27152, 27154, and 27153 between verification engine 27150 and its peer subsystems.

Within verification engine 27150, the functional elements network communication support module 27501, computation resource management module 27502, objects to be verified 27510, test device library 27540, and verification service 27560 may generally be substantially as described in U.S. Pat. No. 8,719,776 with respect to its FIG. 5, where their archetypes are numbered 501, 502, 510, 540, and 560 respectively, although the data handling enhancements described above are incorporated in each of those elements. Similarly, functional elements from FIG. 5 of U.S. Pat. No. 8,719,776 not shown in automatic verification framework 27520, interactive verification framework 27530, and test plan database 27550 are omitted from FIG. 4 for clarity but may be inherited intact from FIG. 5 of U.S. Pat. No. 8,719,776, where they are numbered 520, 530, and 550 respectively. New data handling elements are added for each of those modules as well, as necessary to effect the features of the present embodiments.

Several new modules are introduced in verification engine 27150. Within interactive verification framework 27530, document editor 27533 may provide a coordinator user the ability to annotate or change an automatically generated document. This module may incorporate common text editing tools as well as specializations that facilitate placement and highlighting of captured test results such as screenshots, while removing any ability to alter them materially. Coupled with prior capabilities of this framework to execute and record specific test cases, document editor 27533 may be used to ensure completeness or improve readability of documents generated automatically.

Figure 6:
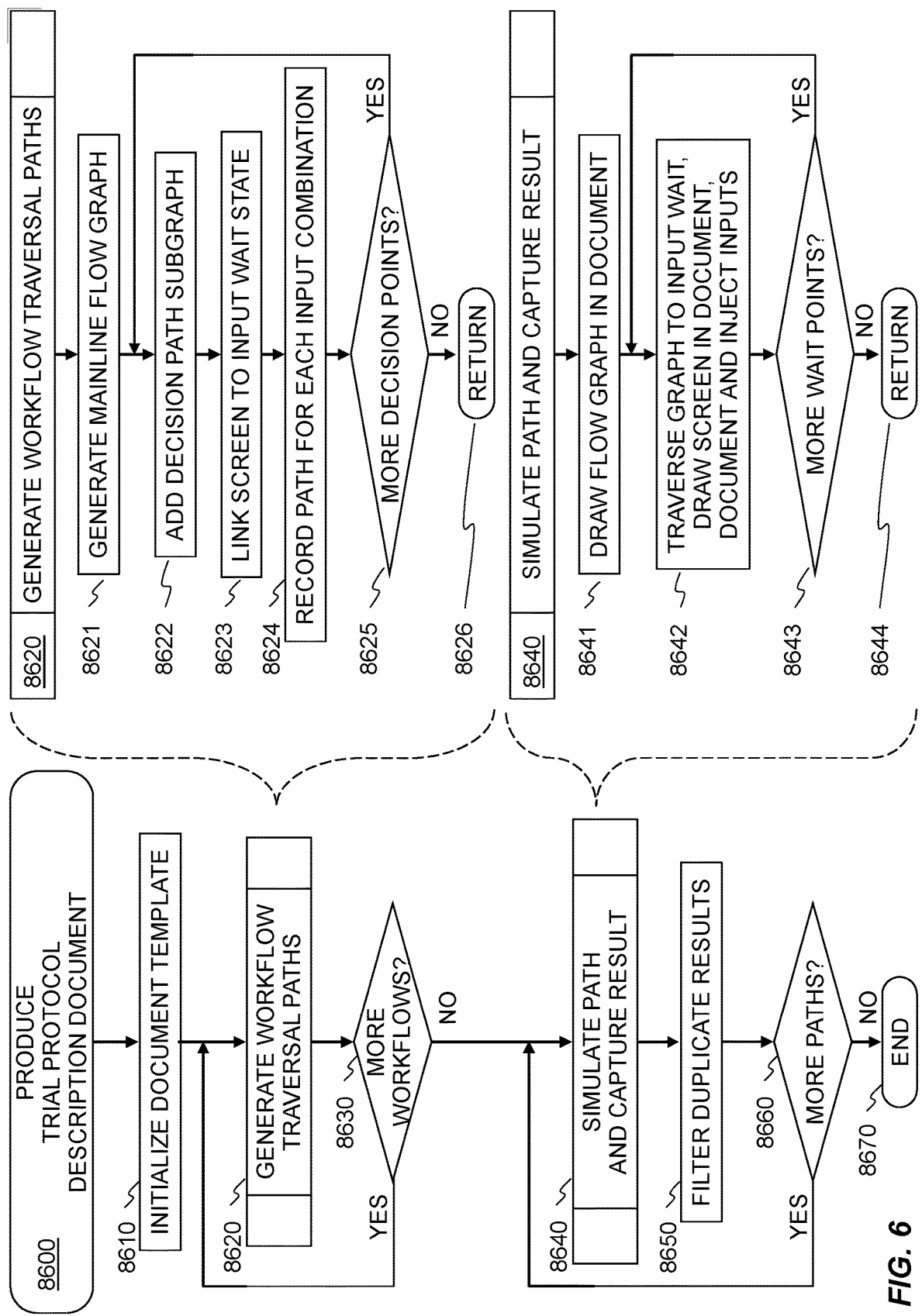
FIG. 6 illustrates an exemplary method whereby a trial operations service suite in a clinical trial operations system may automatically examine the trial design and generate a trial protocol description.

Within automatic verification framework 27520, test case result recorder 27524 augments prior capabilities to drive execution of test cases and analyze their success or failure by capturing in a document the associated inputs, state changes, outputs, and result status. When operated over a series of test cases that exercises every possible path through an application or application component, this record may represent both a complete specification of the object to be verified 27510 and a log of its verification. FIG. 6 and its description depict the process associated with this module.

Within test plan database 27550, coverage tests 27554 may augment the prior tests with cases specifically targeted at executing every logic path in an object to be verified 27510. Such tests may be created by the usual method in application factory system 27100, which is to record a manual test in the interactive verification framework 27530. In addition, coverage tests 27554 may be generated automatically using a specific pass through build engine 27140 (whose details are inherited from U.S. Pat. No. 8,719,776 with respect to its FIG. 4, for example, subsystem linking services, test coverage generator compiler, etc.) in which target device specific language code generator 435 and SDK 440 are selected for the purpose. In this case the precompiled component objects 436 may be existing test case templates, and the SDK 440 may include tools for code coverage tracing and input fuzzing in support of automatic test case generation; such tools have become common for most programming languages and may be incorporated as enhancements not depicted in build engine 27140. The target device specific executable 412 in this case is the set of test cases assembled into a sequence that covers all possible inputs and decisions; when the studio user requests this specific build target, the result may as usual be automatically handed off to verification engine 27150, which in turn may recognize it as a test case set and store it in plan database 27550 under coverage tests 27554.

Also within test plan database 27550, document templates 27555 may provide standard formats for documents that are generated automatically. A coordinator user may select a particular template into which the document generation procedure (see FIG. 6) places its results, thereby allowing for different context, different header information, or different section layout depending on the selected template.

While the examples shown herein may be illustrated as functions, operations, or desired results as individual modules or separate elements, one of ordinary skill in the art would recognize that one or more of these modules may be combined into a single functional block or element. One of ordinary skill in the art would also recognize that a single module may be divided into multiple modules.

III. Methods of Operation

FIG. 5 illustrates a process distributed among a coordinator application, coordinator portal, and other elements of a trial operations service suite in a clinical trial operations system according to an exemplary embodiment of the automatic documentation aspect. Create/edit documentation process 5701 is a variation on coordinator design trial process 5700 in the base patent application(s). Using create/edit documentation process 5701, a coordinator may direct the system 100 to document itself (create) and add or rearrange text in that document (edit). Here again, the three-actor model and temporal/informational interaction conventions used throughout this specification and the base patent application(s) apply. The sub-processes in this case are labeled user actions 5705, application actions 5710, and service actions 5715; the primary service actor is trial design services 271 and the application factory system 27100 embedded in it.

Create/edit documentation process 5701 begins with the prerequisite of coordinator logon process 5500, in which all three actors participate. Coordinator logon process 5500 is not described in the present specification, being inherited from and identical to the process of that name in the base patent application(s). After that, at operation 5720 the coordinator may select trial design services 271 from the menu of coordinator portal services 270. At operation 5735 coordinator application 170 may get the corresponding additional screens and logic from coordinator portal 207, which would at operation 5755 provide a web app implementing the composition studio 27120 of application factory system 27100. At operation 5740, coordinator application 170 may present the screens and controls constituting the user interface of said composition studio 27120, enabling the coordinator at operation 5721 to request automatic document creation. This request may be particularized to indicate either Auto-IRB or Auto-Spec as the document to create, or it may be unparticular causing both document types to be created. The request may also specify a particular template for the document if multiple templates are available from document templates module 27555. Coordinator application 170 then relays the request to the service at operation 5741.

At operation 5761, composition studio 27120 may collaborate with verification engine 27150 as described in the context of FIG. 4 to generate the requested document(s), using the method(s) detailed in FIG. 6 and/or FIG. 7. Once the requested document(s) is/are generated and made available, the document editor 27533 in interactive verification framework 27530 may collaborate with coordinator application 170 so that at operation 5742 the latter may present the document(s) to the coordinator user with controls for annotating and arranging the material. Such controls may take the form of a commonly-available document editing user interface, although the application and service may place constraints on what can be changed in order to preserve the integrity of the automatically generated content and prevent falsifying the actual design. For example, the annotation editor may prevent placement of text or imagery on top of a captured screen image in such a way that the screen content appears altered, and it may prevent deletion of text, allowing only text additions, section rearrangement without separating images from accompanying text, and font adjustments.

In operation 5722, then, the coordinator user may exercise the annotation editor's controls making permitted changes as needed to complete the document according to the goal, for example to satisfy an IRB or other regulatory review. Upon submission of such changes, application 170 may then at operation 5743 relay them to the service, which at operation 5762 may save the changes and produce the final documents for distribution via distribution center 27130. Additional actions that are not depicted may include copying any changes that annotate system behaviors or screen elements back into the corresponding behavior model or screen design source as comments; interpreting any questions placed in annotations as possible bug reports or feature requests and flagging them for developer review via a configuration control subsystem embedded in application factory system 27100, which may be an enhanced function of distribution center 27130 via its library services module 310 as shown in U.S. Pat. No. 8,719,776; and recording version control information associated with the change submission and related actions, which also may utilize a configuration control subsystem embedded as noted in application factory system 27100.

Though not depicted explicitly, iterations over this basic sequence may occur as needed. Once all iterations have been performed, create/edit documentation process 5701 ends with each sub-process quiescing in its own way. User sub-process 5705 simply finishes at operation 5730, with nothing further for the coordinator to do. In application sub-process 5710, coordinator application 170 remains running in coordinator workstation 107, so its quiescent state is waiting for the user's next selection at operation 5750. Similarly, coordinator portal 207 has an established session for this user, with coordinator application 170 connected and authenticated, so it too quiesces in an active state waiting for the next application request at operation 5765. Any of the other coordinator methods may be selected in this state.

FIG. 6 illustrates a method whereby a trial operations service suite in a clinical trial operations system may automatically examine the trial design and generate a trial protocol description suitable for IRB submission. The method may be executed as part of the processing during operation 5761 of create/edit documentation process 5701, described in the context of FIG. 5 above. Produce trial protocol description document method 8600 begins with initialization of a document template at operation 8610. The document template may have been selected by a user as part of operation 5721 of create/edit documentation process 5701, described in the context of FIG. 5 above. Alternatively, the document template may be the only one available in document templates module 27555, or it may be selected automatically by matching a context variable related to one or more trial-specific factors such as corporate or divisional branding, type or phase of study, class of drug, device, or procedure being studied, number of participants, country or language of participants, etc.

IRB documentation describes the trial protocol with respect to its interactions with study subjects so that the board may determine compliance with research ethics, laws, and sound scientific methods. In this context the target document is essentially a specification of patient application 140 covering its screens, inputs, and screen to screen flow. These are all elements of the design as created by a coordinator using trial design services 271, expressed in the visual representation language when shown to the coordinator user in the composition studio, and expressed in the XML-based representation language internally. Method 8600 may document this design by first iterating over the internal representation of the patient application's workflows applying generate workflow traversal paths subroutine 8620 to each one, thereby producing for each workflow a set of paths through it based on the decisions in it and the range of possible inputs that may be provided by the patient user at each decision point. Inputs may include touch or click locations, gestures, character field values entered using a virtual keyboard, numerical values entered using a sliding selector, speech entered via a microphone, or any other piece of information that any sensor may collect under control of the user. Stored data, which may when executing come from a sensor not directly controlled by the user or be provided by an element of patient portal services 240, may also be considered by workflow logic in establishing a path.

When at operation 8630 there are no more workflows left to process in the design for patient application 140, method 8600 may then iterate over the resulting traversal paths applying to each the simulate path and capture result subroutine 8640, thereby inserting into the Auto-IRB document a representation of the path that includes screens displayed and corresponding user inputs.

Figure 9:
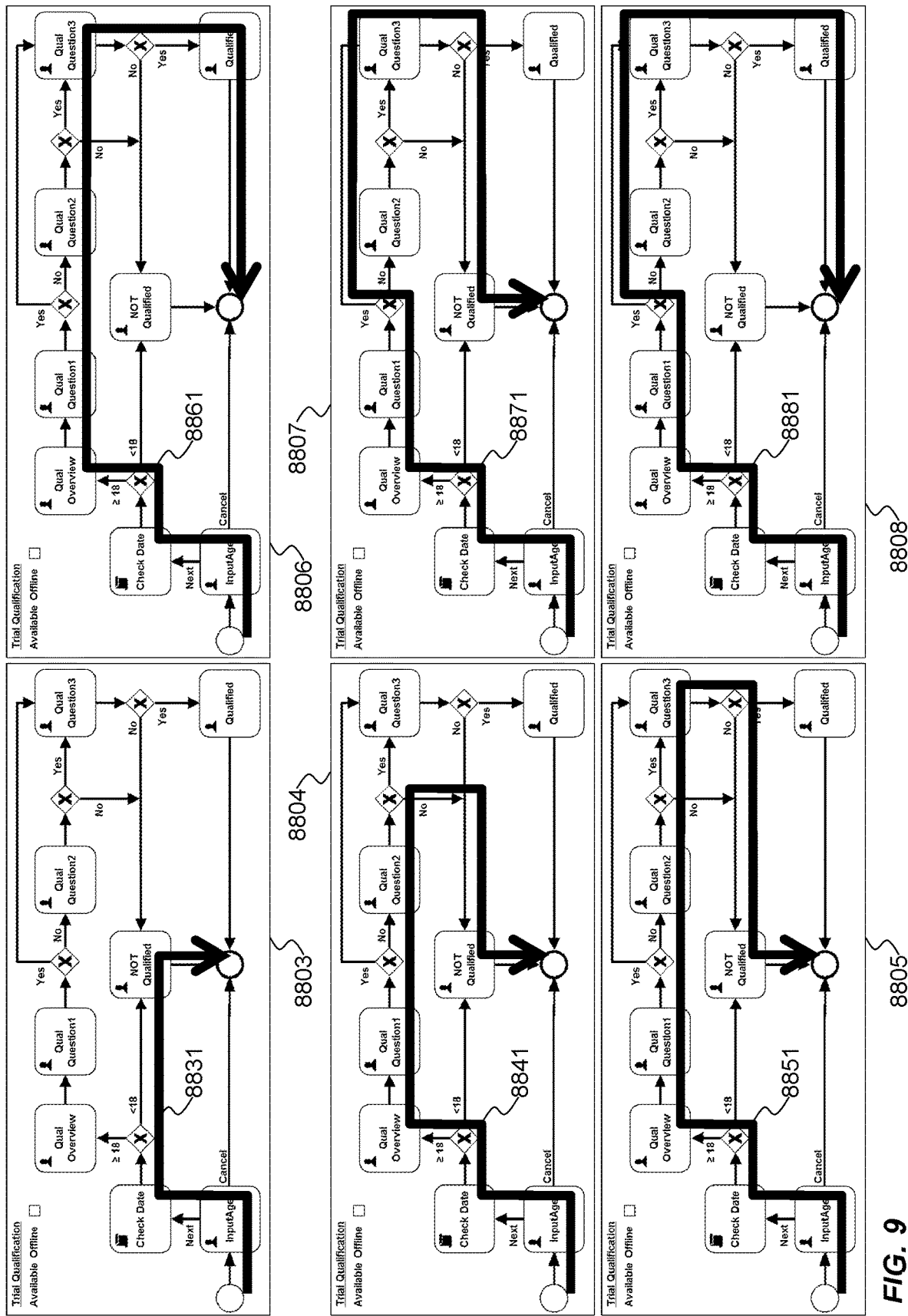

Note that in general, the number of such paths may be quite large due to the range of possible inputs at each decision point, yet for any given workflow the actual number of distinct paths may be relatively small by design. Refer to FIG. 8 and FIG. 9 for an example. Therefore, after processing a path through subroutine 8640, method 8600 may at operation 8650 filter the document for duplicate results in terms of screen content and flow shape. That is, when the resulting document section for a path features the same screens presented in the same order as a path previously accepted into the document, the filter may combine the new section into the previous one by first adding the input set producing the new path to the corresponding input description of the existing path, and then discarding the path and screen images. Detection of a duplicate may apply a variety of techniques with different complexities, from matching identifiers coded with each screen template in the design to recognizing similar images using artificial intelligence algorithms, depending on the intricacy of the actual workflows and screens in the design. Where a screen template contains a field for showing variable output based on a database entry or previous user input, the filter may employ a mask to ignore that field when comparing images. The range of possible techniques is not limited to these examples.

Finally, when at operation 8660 there are no more traversal paths to capture and filter, method 8600 comes to an end at termination point 8670.

Subroutine 8620 generate workflow traversal paths is expanded in FIG. 6 to show its detailed processing. Refer also to FIG. 8 and FIG. 9, which depict an example workflow and its traversal paths. Beginning at operation 8621, the subroutine may generate a graph of the mainline flow associated with the workflow being examined, through to the first decision point—that is, a point in the flow that may branch or continue based on the value of a data item or user input.

At this point the subroutine enters a block of operations that may be repeated for every such decision point in every branch of the workflow. At operation 8622 a subgraph may be constructed for the subflow or subflows that may follow from the decision point at hand; these are then added to the overall flow graph. At operation 22023 any screen that may be associated with this decision point, if it is a wait state at which user input may be expected, may be linked to the flow graph at this point. Operation 8624 examines the expected user input(s) and data items on which this decision point depends, analyzes the logic encoded in the workflow at this point, constructs the set of possible combinations that may occur, and then records a distinct path through the flow associated with each of the input combinations. As part of recording a path, its input and data combinations may be generalized into range combinations in order to reduce the number of discrete path entries created; every value in each range combination so generalized would follow the same path and/or display the same screen as a result. To the extent this operation can generalize range combinations, the number of paths recorded may be reduced, in turn lightening the load on (and corresponding complexity of) the duplicate results filter in operation 8650 of the main method 8600.

When operation 8625 determines that the workflow has no more decision points to analyze, subroutine 8620 reaches its end and returns via operation 8626 to the main method.

Subroutine 8640 simulate path and capture result is expanded in FIG. 6 to show its detailed processing. Beginning at operation 8641, the subroutine may draw into the document the flow graph associated with the traversal path at hand. The procedure for drawing may be parameterized such that the size of the resulting diagram is scaled to be readable. For example, if only a few screens and transitions occur in the flow a single diagram on a single page may be produced, but beyond a threshold multiple diagrams linked across multiple pages may be produced. The threshold may be as simple as a single parameter controlling the number of screens that maybe shown on one page; this parameter may be tunable by a coordinator user as part of the trial design or document creation request, or set to a default value in the implementation of this method. More complex parameterizations may also be applied, such as one depending on both the number of screens and the number of branches from each screen based on the variety of user inputs required on each screen.

Once the main flow has been drawn, the subroutine enters a block of operations that may be repeated for every decision point or user input wait state in every branch of the path. At operation 8642 a simulation of the path is executed that traverses the path's flow graph to an input wait point. If any decisions are made along the way based on data that is not taken from user input, these are documented as well by noting the data values that cause the flow to follow this particular path. The screen associated with this input wait is then drawn into the document at the appropriate point along the flow graph drawing, and annotated with the input values used at this point in this particular path. Those inputs are then injected into the simulation. As long as operation 8643 determines that there are more wait points to be examined in the path, operation 8642 is repeated for each one. When all branches of the path have been traversed and captured in the document, operation 8643 drops out of the loop and the subroutine ends at operation 8644 by returning to the main method.

FIG. 7 illustrates a method whereby a trial operations service suite in a clinical trial operations system may automatically examine the trial design and generate a software specification for the service suite itself and the applications that interact with it. The method may be executed as part of the processing during operation 5761 of create/edit documentation process 5701, described in the context of FIG. 5 above. Produce system specification document method 8700 begins with initialization of a document template at operation 8710. The document template may have been selected by a user as part of operation 5721 of create/edit documentation process 5701, described in the context of FIG. 5 above. Alternatively, the document template may be the only one available in document templates module 27555, or it may be selected automatically by matching a context variable related to one or more specific factors such as corporate or divisional branding, whether certain gateways and services are enabled or disabled, country or language of the coordinator, etc.

A system specification describes the entire clinical trial operations system 100, including all aspects of the trial operations service and each application. In this context the target document is a superset of the Auto-IRB document, covering not just patient application 140 but also clinician application 150, investigator application 160, coordinator application 170, and trial operations service suite 200. Further, where the Auto-IRB document covers only the patient-facing aspects of patient application 140, the Auto-Spec document also covers service-facing aspects such as interactions between application and portal—both behaviors and data structures. In general, anything in the system may be changed by a coordinator using trial design services 271, but in practice very little is likely to be customized except patient application 140. Therefore, the Auto-Spec template may provide a much larger portion of the actual specification in this case. For services, gateways, and analytics in particular, the primary customizations may simply be to enable or disable particular features. Template initialization at operation 8710 may take this into consideration by removing entire sections for disabled features.

The remainder of produce system specification document method 8700 may then be very similar to produce trial protocol description document method 8600, with an additional loop to cover the other system elements. That is, method 8600 may document the customizations made in each element of the system by first iterating over the internal representation of workflows and logic for each application, portal service, relay service, gateway, and analytics module, applying generate workflow traversal paths subroutine 8620 to each one, thereby producing for each workflow a set of paths through it based on the decisions in it and the range of possible inputs that may be provided by a user at each decision point. Inputs may include touch or click locations, gestures, character field values entered using a virtual keyboard, numerical values entered using a sliding selector, speech entered via a microphone, or any other piece of information that any sensor may collect under control of the user. Stored data, which in an executing application may come from a sensor not directly controlled by the user or be provided by an element of its corresponding portal, and which in an executing element of trial operations service suite 200 may come from operational databases 202 or security configuration and management authentication database 201, may also be considered by workflow logic in establishing a path.

In addition to generating the traversal paths for each workflow in the system, any data schemata associated with the workflow at hand are recorded at operation 8720. This ensures that database tables and fields used in the workflow and its logic are documented, as well as data structures for inter-process and inter-element communication, user notifications, and inter-system communication via gateways.

When at operation 8730 there are no more workflows left to process in the design for the element at hand, and at operation 8735 there are no more applications, services, gateways, or analytics modules left to process in the design for the system, method 8700 may then iterate over the resulting traversal paths applying to each the simulate path and capture result subroutine 8640, thereby inserting into the Auto-Spec document a representation of the path that includes screens displayed and corresponding user inputs, plus additional information captured along the way including the aforementioned data schemata.

Note that in general, the number of such paths may be quite large due to the range of possible inputs at each decision point, yet for any given workflow the actual number of distinct paths may be relatively small by design. Therefore, after processing a path through subroutine 8640, method 8700 may at operation 8750 filter the document for duplicate results in terms of screen content and flow shape, as well as in terms of data schemata content or shape where appropriate, such as in an element with inter-process, inter-element, or inter-system communication behaviors. Similar comparison techniques may be applied here as previously described for operation 8650 in method 8600.

Finally, when at operation 8760 there are no more traversal paths to capture and filter, method 8700 comes to an end at termination point 8770.

One skilled in the art may observe that the resulting document is not a specification in the traditional sense—a relatively compact set of requirements for what the system should do. Instead, because the embedded application factory system 27100 enables the system's design and implementation to be conflated, it is actually a description, using the specification form, of what the system does. Thus, the Auto-Spec document may be used for oversight to understand the system, but it will not be needed for driving a development project separate from the design project. That latter endeavor having been eliminated entirely by this technology is the primary benefit of the embodiments in both the base and present patent applications.

FIG. 8 and FIG. 9 illustrate an exemplary workflow and its traversal paths as may be generated by subroutine 8620 generate workflow traversal paths. Example work flow 8801 depicts what may be a structure for a participant qualification workflow, wherein a patient candidate may determine whether he or she is a fit for a specific clinical trial supported by a particular instance of system 100. Note that the associated user interface screens for example workflow 8801 are not depicted, but would certainly exist and be processed by methods 8600 and 8700, having been created using the visual language described in the context of example user interface 390 in FIG. 3. One skilled in the art will recognize the visual language of example workflow 8801 from its earlier explication using example workflow 380 in FIG. 3, so the detailed flow is not described further other than to point out that example workflow 8801 has a richer structure with more decision points than example workflow 380, and is thereby more suitable for depicting a variety of traversal paths.

Example workflow 8801 is duplicated in miniature as example workflow copy 8802, onto which traversal path 8821 is overlaid as a heavy arrow flowing from its start symbol to its end symbol through the first decision point in the flow. FIG. 9 then depicts six more miniature copies of example workflow 8801, shown as example workflow copies 8803, 8804, 8805, 8806, 8807, and 8808. These are in turn overlain by their respective traversal paths 8831, 8841, 8851, 8861, 8871, and 8881. Thus subroutine 8620 generate workflow traversal paths would record seven distinct traversal paths during its execution over example workflow 8801, covering every possible branch through the workflow based on different user inputs or calculated outcomes at each decision point.

The processes of FIG. 5 through FIG. 9 may be implemented in various different ways without departing from the scope of the disclosure. For instance, the operations may be performed in different orders than shown. As another example, some processes may include additional operations and/or omit various listed operations.

While the examples shown may illustrate many individual modules (or operation sets, performed by software instructions and/or user, clinician, operator, etc. action) as separate elements, one of ordinary skill in the art would recognize that these modules may be combined into a single functional block or element. One of ordinary skill in the art would also recognize that a single module may be divided into multiple modules. Further, the steps, operation sets, functions, etc. described in the various modules are understood to be actionable via a computer or processor executing instructions, to provide the features and results described herein. Thus, one of ordinary skill in the computer and software arts, having read this disclosure, could devise and replicate the features of the various modules, as well as modifications within the scope of this disclosure without undue experimentation.

IV. Computer System

Many of the processes and modules described above may be implemented as software processes that are specified as one or more sets of instructions recorded on a non-transitory storage medium. When these instructions are executed by one or more computational element(s) (e.g., microprocessors, microcontrollers, digital signal processors (DSPs), application-specific integrated circuits (ASICs), field programmable gate arrays (FPGAs), etc.) the instructions cause the computational element(s) to perform actions specified in the instructions.

In some embodiments, various processes and modules described above may be implemented completely using electronic circuitry that may include various sets of devices or elements (e.g., sensors, logic gates, analog to digital converters, digital to analog converters, comparators, etc.). Such circuitry may be able to perform functions and/or features that may be associated with various software elements described throughout.

FIG. 78 in the base patent application(s) illustrates a schematic block diagram of an exemplary computer system 7800 used to implement some embodiments. For example, the systems described above in reference to FIG. 1 through FIG. 4 may be at least partially implemented using computer system 7800. As another example, the processes described in reference to FIG. 5 through FIG. 9 may be at least partially implemented using sets of instructions that are executed using computer system 7800.

Computer system 7800 may be implemented using various appropriate devices. For instance, the computer system may be implemented using one or more personal computers (PCs), servers, mobile devices (e.g., a smartphone), tablet devices, and/or any other appropriate devices. The various devices may work alone (e.g., the computer system may be implemented as a single PC) or in conjunction (e.g., some components of the computer system may be provided by a mobile device while other components are provided by a tablet device).

FIG. 78 of the base patent application(s) and computer system 7800 are considered to be incorporated in the present patent application by reference, and therefore are not detailed here.

As used in this specification and any claims of this application, the terms "computer", "server", "processor", and "memory" all refer to electronic devices. These terms exclude people or groups of people. As used in this specification and any claims of this application, the term "non-transitory storage medium" is entirely restricted to tangible, physical objects that store information in a form that is readable by electronic devices. These terms exclude any wireless or other ephemeral signals.

It should be recognized by one of ordinary skill in the art that any or all of the components of computer system 7800 may be used in conjunction with some embodiments. Moreover, one of ordinary skill in the art will appreciate that many other system configurations may also be used in conjunction with some embodiments or components of some embodiments.

In addition, while the examples shown may illustrate many individual modules as separate elements, one of ordinary skill in the art would recognize that these modules may be combined into a single functional block or element. One of ordinary skill in the art would also recognize that a single module may be divided into multiple modules.

The foregoing relates to illustrative details of exemplary embodiments and modifications may be made without departing from the scope of the disclosure as defined by the following claims.

What is claimed is:

1. A system, comprising:
   one or more computational elements; and
   a non-transitory storage medium including instructions executable by the one or more computational elements to configure the one or more computational elements to:
   provide a coordinator-customized patient application configured to access a patient portal generated using a trial design services module, for providing patient information for a clinical trial;
   iterate over a representation of workflows and logic for each application, portal service, relay service, gateway, and analytics module of the coordinator-customized patient application, traversal paths through each workflow, based on decision points in the workflow and a range of possible inputs that may be provided by a user at each decision point of the decision points;
   in response to iterating traversal paths over workflows in the representation of workflows, iterate a simulated path over resulting traversal paths applying to each workflow; and
   insert into an institutional review board document, a representation of any traversal path that includes user screens and corresponding user inputs as determined by the simulated path.

2. The system of claim 1, wherein the instructions are executable by the one or more computational elements to selectively generate an entire specification document describing a design of an entire clinical trial operations system.

3. The system of claim 1, wherein the trial design services module comprises an application factory system that automatically generates via a workflow palette and a composition studio's visual programming toolkit, the user screens for the clinical trial.

4. The system of claim 3, wherein the application factory system comprises:

an automatic verification framework with a test case result recorder, configured to capture in a specification document, associated inputs, state changes, outputs, and result status for test cases;
a test plan database including coverage tests with cases targeted at executing at least some of the logic in an object to be verified and a plurality of document templates, containing standard formats for documents that are generated automatically;
an interactive verification framework with a document editor and supporting user interface;
a test device library containing testable device models;
application objects and application components to be verified; and
a verification service which verifies the application objects and application components.

5. The system of claim 4, further comprising, a build engine with compilation and subsystem linking services.

6. The system of claim 5, wherein the build engine uses a test coverage generator as a compiler.

7. The system of claim 4, further comprising, a composition studio providing an ability to develop applications and the application components.

8. The system of claim 7, further comprising, a document creation request control.

9. The system of claim 7, wherein the composition studio utilizes a multimedia user interface design toolkit and programming design toolkit.

10. A non-transitory storage medium including instructions executable by one or more computational elements to perform operations comprising:
    providing a coordinator-customized patient application configured to access a patient portal generated using a trial design services module, for providing patient information for a clinical trial ;
    iterating over a representation of workflows and logic for each application, portal service, relay service, gateway, and analytics module of the coordinator-customized patient application, traversal paths through each workflow, based on decision points in the workflow and a range of possible inputs that may be provided by a user at each decision point of the decision points;
    in response to iterating traversal paths over workflows in the representation of workflows, iterating a simulated path over resulting traversal paths applying to each workflow; and
    inserting into an institutional review board document, a representation of any traversal path that includes user screens and corresponding user inputs as determined by the simulated path.

11. The non-transitory storage medium of claim 10, wherein the operations further comprise selectively generating an entire specification document describing a design of an entire trial.

12. The non-transitory storage medium of claim 10, wherein the operations further comprise generating, using a workflow palette and a composition studio's visual programming toolkit, the user screens for the clinical trial.

13. The non-transitory storage medium of claim 12, wherein the operations further comprise:
    capturing in a specification document, associated inputs, state changes, outputs, and result status for test cases;
    executing at least some of the logic in an object to be verified;
    accessing an interactive verification framework with a document editor and supporting user interface to edit the specification document;

using a test device library containing testable device models to test at least one device model;

verifying application objects and application components; and verifying the application objects and application components.

14. The non-transitory storage medium of claim 13, wherein the operations further comprise, providing compilation and subsystem linking services using a build engine.

15. The non-transitory storage medium of claim 14, wherein the build engine uses a test coverage generator as a compiler.

16. The non-transitory storage medium of claim 13, wherein the operations further comprise, providing a composition studio configured to provide an ability to develop applications and the application components.

17. The non-transitory storage medium of claim 16, wherein the operations further comprise, providing a document creation request control.

18. The non-transitory storage medium of claim 16, wherein the composition studio utilizes a multimedia user interface design toolkit and programming design toolkit.

* * * * *